(12) United States Patent
Zhao et al.

(10) Patent No.: US 8,194,301 B2
(45) Date of Patent: Jun. 5, 2012

(54) MULTI-SPOT SCANNING SYSTEM AND METHOD

(75) Inventors: Guoheng Zhao, Milpitas, CA (US); Rex Runyon, Fremont, CA (US); Mehdi Vaez-Iravani, Los Gatos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 974 days.

(21) Appl. No.: 12/042,252

(22) Filed: Mar. 4, 2008

(65) Prior Publication Data

US 2009/0225399 A1 Sep. 10, 2009

(51) Int. Cl.
*G02B 26/08* (2006.01)

(52) U.S. Cl. .................................. 359/204.1; 359/900

(58) Field of Classification Search .... 359/204.1–204.5, 359/216.1–219.2; 347/232–261
See application file for complete search history.

(56) References Cited

U.S. PATENT DOCUMENTS

| | | | |
|---|---|---|---|
| 5,748,223 A * | 5/1998 | Ito | 347/241 |
| 6,208,411 B1 | 3/2001 | Vaez-Iravani | |
| 6,248,988 B1 | 6/2001 | Krantz | |
| 6,671,042 B1 | 12/2003 | Almogy | |
| 7,049,155 B2 | 5/2006 | Reinhorn | |
| 7,130,039 B2 | 10/2006 | Vaez-Iravani et al. | |
| 7,164,515 B2 * | 1/2007 | Ito et al. | 359/204.1 |
| 2006/0197946 A1 | 9/2006 | Biellak et al. | |

* cited by examiner

*Primary Examiner* — James Phan
(74) *Attorney, Agent, or Firm* — Bever, Hoffman & Harms, LLP; Jeanette S. Harms

(57) ABSTRACT

A multi-spot scanning technique using a spot array having a predetermined gap between spots can advantageously provide scalability to a large number of spots as well as the elimination of cross-talk between channels. The multi-spot scanning technique can select a number of spots for the spot array (1D or 2D), determine a separation between the spots to minimize crosstalk, and perform a scan on a wafer using the spot array and a full field of view (FOV). Performing the scan includes performing a plurality of scan line cycles, wherein each scan line cycle can fill in gaps left by previous scan line cycles. This "delay and fill" scan allows large spacing between spots, thereby eliminating cross-talk at the detector plane. In one embodiment, the scan is begun and ended outside a desired scan area on the wafer to ensure full scan coverage.

8 Claims, 18 Drawing Sheets

FIG. 7C

Table 730 — Spot index i (Swath index j) vs. Spot separation M (Number of spots N)

Hatched cells are shown in bold.

| i \ j | 1 | 2 | 3 | 4 | 5 | 6 | 7 | 8 | 9 | 10 | 11 | 12 | 13 | 14 | 15 | ... |
|---|---|---|---|---|---|---|---|---|---|---|---|---|---|---|---|---|
| 16 | 16 | 31 | 46 | 61 | 76 | 91 | 106 | 121 | 136 | 151 | 166 | 181 | 196 | 211 | 226 | ... |
| 15 | 15 | 29 | 43 | 57 | 71 | 85 | 99 | 113 | 127 | 141 | 155 | 169 | 183 | 197 | 211 | ... |
| 14 | 14 | 27 | 40 | 53 | 66 | 79 | 92 | 105 | 118 | 131 | 144 | 157 | 170 | 183 | 196 | ... |
| 13 | 13 | 25 | 37 | 49 | 61 | 73 | 85 | 97 | 109 | 121 | 133 | 145 | 157 | 169 | 181 | ... |
| 12 | 12 | 23 | 34 | 45 | 56 | 67 | 78 | 89 | 100 | 111 | 122 | 133 | 144 | 155 | 166 | ... |
| 11 | 11 | 21 | 31 | 41 | 51 | 61 | 71 | 81 | 91 | 101 | 111 | 122 | 131 | 141 | 151 | ... |
| 10 | 10 | 19 | 28 | 37 | 46 | 55 | 64 | 73 | 82 | 91 | 100 | 109 | 118 | 127 | 136 | ... |
| 9 | 9 | 17 | 25 | 33 | 41 | 49 | 57 | 65 | 73 | 81 | 89 | 97 | 105 | 113 | 121 | ... |
| 8 | 8 | 15 | 22 | 29 | 36 | 43 | 50 | 57 | 64 | 71 | 78 | 85 | 92 | 99 | 106 | ... |
| 7 | 7 | 13 | 19 | 25 | 31 | 37 | 43 | 49 | 55 | 61 | 67 | 73 | 79 | 85 | 91 | ... |
| 6 | 6 | 11 | 16 | 21 | 26 | 31 | 36 | 41 | 46 | 51 | 56 | 61 | 66 | 71 | 76 | ... |
| 5 | 5 | 9 | 13 | 17 | 21 | 25 | 29 | 33 | 37 | 41 | 45 | 49 | 53 | 57 | 61 | ... |
| 4 | 4 | 7 | 10 | 13 | 16 | 19 | 22 | 25 | 28 | 31 | 34 | 37 | 40 | 43 | 46 | ... |
| 3 | 3 | 5 | 7 | 9 | 11 | 13 | 15 | 17 | 19 | 21 | 23 | 25 | 27 | 29 | 31 | ... |
| 2 | 2 | 3 | 4 | 5 | 6 | 7 | 8 | 9 | 10 | 11 | 12 | 13 | 14 | 15 | 16 | ... |
| 1 | 1 | 1 | 1 | 1 | 1 | 1 | 1 | 1 | 1 | 1 | 1 | 1 | 1 | 1 | 1 | ... |

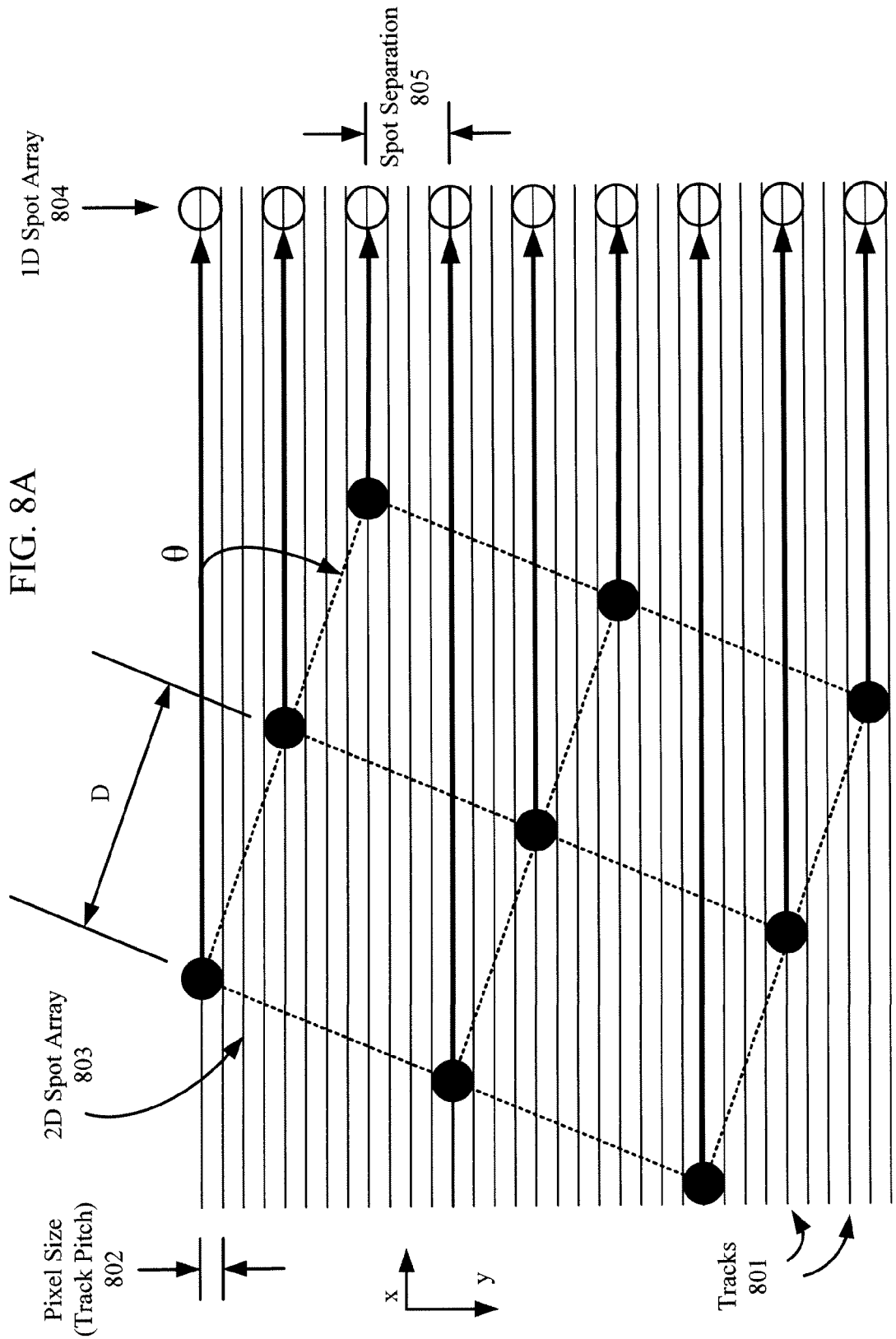

MULTI-SPOT SCANNING SYSTEM AND METHOD

BACKGROUND OF THE INVENTION

1. Field of the Invention

The present invention relates to wafer inspection and in particular to a multi-spot scanning technique using a spot array having gaps between the spots to achieve high speed and high sensitivity wafer inspection with minimum cross-talk between spots.

2. Related Art

Many prior art inspection systems have used a single spot to scan a wafer surface. Unfortunately, the data rate of a single channel (i.e. single spot) is typically limited to be less than 200 megapixels per second (MPPS). However, for the next generation inspection systems, the total data rate is required to be more than 10 gigapixels per second (GPPS), which requires at least 50 channels.

Various multi-spot inspection systems have been proposed to overcome the limited data rate of the single spot inspection systems. For example, U.S. Pat. No. 6,236,454 teaches a multi-beam inspection system 100, which is shown in FIG. 1. Multi-beam inspection system 100 includes a multi-beam laser scanning system 101 that generates multiple beams (and thus multiple spots) that are scanned across a sample (e.g. a wafer) 107 and a multi-beam imaging system 102 that collects the light scattered by sample 107 from such scanning. In general, multi-beam laser scanning system 101 includes a beam generator 103 (multiple lasers or a single laser with multiple beam splitters) to generate the multiple beams, pre-scan optics 104 that provide the beams with the desired optical properties, one or more scan units 105 that deflect the beams to provide the scanning motion, and an objective lens 106 that focuses the scanning beams on sample 107.

Due to the motion of scan unit(s) 105, the focused beams move in a first direction. Typically, sample 107 is moved in a second direction orthogonal to the first direction. The first and second directions allow inspection system 100 to provide two-dimensional scanning. The scanning rate (e.g. spots/sec) is a function of the spot velocity and spot size (both functions of scan unit(s) 105).

Multi-beam imaging system 102 includes collection optics 108 and photodetectors 109. Collection optics 108 can be a single lens or multiple optical components. Photodetectors are placed in an image plane near the location where the scan lines of the scanned beams are imaged by collection optics 108.

FIG. 2 illustrates two scans 201A and 201B performed on a wafer surface 200. Note that each scan 201A and 201B is formed by a plurality of first movements 202 (due to scan unit(s) 105) and a plurality of second movements 203 (due to the moving of sample 107). The first movements 202 define a scan line comprising a plurality of spots, each spot having a scan field. Note that any gaps in the scan area (e.g. the gap between scans 201A and 201B) can be filled by using another round of scan.

Specifically, in multi-beam inspection system 100, the optical field of view (FOV) is equally divided by the number of spots, and the width of the scan field of each spot is one-half of the divided optical field. Such arrangement ensures that the residual light scattered from one spot does not enter the collection channels of the other spots, thereby allowing a clean separation of the spots at photodetectors 109 (i.e. the detector plane).

Unfortunately, multi-beam inspection system 100 has two significant limitations. As a first disadvantage, the effective field of view (FOV) is a factor $N/(2N-1)$ of the available FOV of the scan optics, where N is the number of spots. When N is large, the effective FOV is approximately only one-half of the FOV of scan optics 106 (i.e. the objective lens). That is, at any point in time during the scan, only one-half of the FOV is being used. (Note that although the FOV in FIG. 2 is shown as being 3× the scan line length for 2 spots, actual FOVs in actual wafers could be much wider. Thus, the FOV in FIG. 2 is merely to emphasize the use ratio.) For higher resolution inspection, a large objective lens is used to provide the FOV. This large objective lens is difficult and expensive to manufacture. Thus, the above-described scanning effectively wastes the actual FOV (provided by a high resolution objective lens).

As a second disadvantage, the FOV of the objective lens 106 is physically limited, especially at very high resolution. As a result of the physical limitations of the optics, the scan field of each spot decreases as the number of spots increases, which for any given data rate results in the increase of both line frequency (i.e. the first movements 202) and the stage speed (i.e. the second movements 203). Unfortunately, this increase in line frequency and stage speed requires very expensive electronics and is subject to the physical limits of stage speed and scanner frequency. Therefore, multi-beam inspection system 100 is typically limited to a small number of spots (for example, less than 10). However, as noted above, this limited number of spots (i.e. channels) is not suitable for high data rate (high speed) inspection.

U.S. Pat. No. 6,636,301, issued to KLA-Tencor, teaches a method of multi-beam inspection that eliminates the inefficiency of using the optics FOV by offsetting the spots in two directions. Specifically, as shown in FIG. 3A, spots 301A, 301B, and 301C are offset in both vertical and horizontal directions from each other. Note that each spot 301A, 301B, and 301C has a scanning length L that forms a scanning stripe 302A, 302B, and 302C, respectively (in the vertical direction). The scanning stripes 302A, 302B, and 302C form a swatch S. In the vertical direction, spots 301A, 301B, and 301C are offset by approximately L (e.g. scanning length L minus an overlap portion O). In the horizontal direction, spots 301A, 301B, and 301C are offset by distance W.

As shown in FIG. 3B, spots 301A, 301B, and 301C, and more specifically stripes 302A, 302B, and 302C, are moved across a wafer surface in serpentine patterns 310 (solid line), 311 (dashed line), and 312 (dotted line), respectively. Notably, the described offsets allow the spots to be separated at the detector plane without leaving gaps between the scan fields of each spot. Although this method eliminates the inefficiency of utilizing the optics FOV, it still divides the optical FOV among the spots, which is subject to the limitation of scanner line rate and stage speed. Therefore, this inspection system with both vertical and horizontal spot offset is also typically suitable for only a small number of spots.

U.S. Pat. No. 7,049,155 teaches a multi-beam inspection system that uses a scan pattern non-perpendicular to the wafer movement. Specifically, FIG. 4 illustrates five scans of a multi-beam scan pattern with four beams, thereby generating 20 scan lines 401 (return scan lines 402 shown for reference). Notably, the scan pattern is not perpendicular to a direction S (i.e. the movement of the wafer). Note that D represents the distance between scan lines 401, whereas T represents the distance between scan lines in the mechanical scanning direction.

FOV 403 represents the horizontal field of view (FOV) of the multi-beam inspection system, which like other prior art systems, divides its FOV by the number of spots (in this case, four spots) and is, therefore, limited to having a small number of spots. Note that the separation of spots at the detectors can be achieved by tilting the scan direction away from the perpendicular to direction S. However, the angle of tilt is also determined by the scan line rate and stage speed, which has limited flexibility. Therefore, this multi-beam inspection system also has a number of significant disadvantages.

U.S. Pat. No. 7,130,039 teaches a multi-spot inspection imaging system that uses an array of illuminated spots. FIG. 5A illustrates an exemplary multi-spot array 501 that is slightly rotated with respect to the tangential direction Q of the wafer as the wafer is rotated. Note that the spots in multi-spot array 501 "paint" adjacent tracks. For example, FIG. 5B illustrates adjacent spots 502 and 503 traveling along tracks 504 and 505, respectively. Tracks 504 and 505 may be offset by a separation equal to one-third or one-quarter of the spot size to achieve a desired sampling level (e.g. 3×3 or 4×4 samples per spot width) (thus, spots 502 and 503 overlap by two-thirds or three-quarters of the spot size). Thus, a 1D scan of the wafer produces a 2D image with no gap between tracks. For inspection analysis, the resulting cross-talk from this scan must be "undone" to separate the spots at the detector plane.

As demonstrated from the above-described inspection systems, although the generation of multiple spots to illuminate a sample (e.g. a wafer) is relatively straightforward, such systems typically limit the number of spots, the speed of the scanner, and/or the speed of stage to yield accurate results. Therefore, a need arises for a multi-spot inspection system that can provide a high data rate commensurate with the next generation of inspection system requirements.

SUMMARY OF THE INVENTION

Conventional multi-spot scanning techniques typically use only a few spots to ensure separation of those spots at the detector plane. Moreover, conventional multi-spot scanning techniques typically divide the optical field of view (FOV) by the number of spots, thereby requiring expensive electronics to provide the fast (and uneven) movements of the scanner and the stage. Moreover, using only a portion of the FOV during a scan line cycle inefficiently uses the expensive optics in the scanning system. As a result of these limitations, conventional multi-spot scanning techniques cannot be used to provide the high data rates commensurate with the next generation of inspection system requirements in a cost-effective manner.

A multi-spot scanning technique using a spot array having a predetermined gap between spots can advantageously provide scalability to a large number of spots as well as the elimination of cross-talk between channels. To provide these advantages, the multi-spot scanning technique can select a number of spots N for the spot array, determine a separation M between the spots to minimize crosstalk, and perform a scan on a wafer using the spot array and a full field of view (FOV). The spot array can be one-dimensional (1D) or two-dimensional (2D).

Performing the scan includes performing a plurality of scan line cycles, wherein each scan line cycle can fill in gaps left by previous scan line cycles. This "delay and fill" scan allows large spacing between spots, thereby eliminating cross-talk at the detector plane. In one embodiment, the scan is begun and ended outside a desired scan area on the wafer to ensure full scan coverage.

Notably, a complete scan can be performed without overlapping/missing tracks by providing that (1) a pitch of the swath of the array equals the number of spots N and (2)

$$\frac{M}{j-1} \neq \frac{N}{i-1},$$

where i=2, 3, ... N and j=2, 3, ... M. In one embodiment, a table or a chart can be used to determine allowable combinations of M and N.

In one 2D spot array embodiment, the separation M refers to a separation between groups of spots in the 2D spot array. However, once again, a scan on the wafer can be performed using the 2D spot array and a full field of view (FOV) for each scan line cycle.

A multi-spot scanning system that can perform the above-described steps can include a spot array generator, a scanner, an objective lens, a stage, and a plurality of detection arrays. The spot array generator can be configured to provide a number of spots N for a spot array and to determine a separation M between the spots in the spot array to minimize crosstalk. The scanner can receive the spot array and move the spot array in a first direction (e.g. in an "x" direction). The objective lens, which has a FOV, can focus the moving spot array onto a wafer. The stage can move the wafer in a second direction (e.g. the "y" direction). The detection arrays can receive the light that impinges on the wafer. As indicated above, the scanner can advantageously move the spot array using a full FOV and can use multiple scan line cycles to fill in gaps left by previous scan line cycles. Note that in one 2D embodiment, the separation M can refer to the separation between groups of spots.

In one embodiment, a multi-spot scanning system can include a spot array generator, an objective lens, a spindle, a stage, and detector arrays. The spot array generator can be configured to provide a number of spots N for the spot array and to determine a separation M between the spots to minimize crosstalk. The objective lens can focus the moving spot array onto the wafer, wherein notably the objective lens has a field of view (FOV). The spindle can receive the wafer and move it in a circular direction. The stage can move the wafer in a linear direction when the spindle is moving the wafer in the circular direction. The detection arrays can receive the light impinging on the wafer. Notably, the combination of the linear direction and the circular direction result in the spot array moving relative to the wafer. Specifically, the spot array uses a full FOV and uses multiple scan line cycles to fill in gaps left by previous scan line cycles.

These multi-spot scanning systems can advantageously provide both a high speed as well as a high efficiency scan. That is, the throughput of the scan can be optimized without compromise on the quality of the detection results. Moreover, using the full FOV of the optics during each scan cycle advantageously leverages the expensive optics in the scanning system.

BRIEF DESCRIPTION OF THE FIGURES

FIGS. 7C and 7D illustrate a table that can indicate allowable combinations of the number of spots N and the number of gap tracks M. Exemplary combinations for N and M are used in the table.

FIG. 8A illustrates an exemplary 2D spot array and its equivalent 1D spot array.

DETAILED DESCRIPTION OF THE FIGURES

A common characteristic of all the existing multi-spot scans (using either a 1D spot array or a 2D spot array) is that gaps between adjacent scan tracks are not allowed. That is, the distance between any two adjacent tracks from two consecutive scans of the spot array is exactly the same as the pixel size. This characteristic places stringent constraints on the spot layout, which makes it very difficult to separate the spots at the detector plane.

Various attempts have been made to get around this constraint, which all result in a compromise in performance and speed. For example, in a conventional 1D spot array, the number of spots is typically limited to a small number (e.g. <10), which is not suitable for future high speed, high resolution inspection. Moreover, because the optical FOV is divided equally by the number of spots, a very high speed scanner is required. For these reasons, a clean separation of spots is difficult, and often can only be obtained with a trade-off of scan efficiency, light efficiency, and/or cross-talk between the channels. Similarly, in a conventional 2D spot array, the separation of spots is determined by the total number of spots and track pitch, which may not be large enough for minimal cross-talk at high resolution.

In contrast, and described below in detail, an improved multi-spot scan using a spot array having gaps between the spots can advantageously scale to a large number of spots. Therefore, even when the scanner and the stage operate at moderate speeds, the resulting throughput is still significantly increased compared to prior art scans. Moreover, these gaps can eliminate cross-talk on the detector plane.

Figure 1:
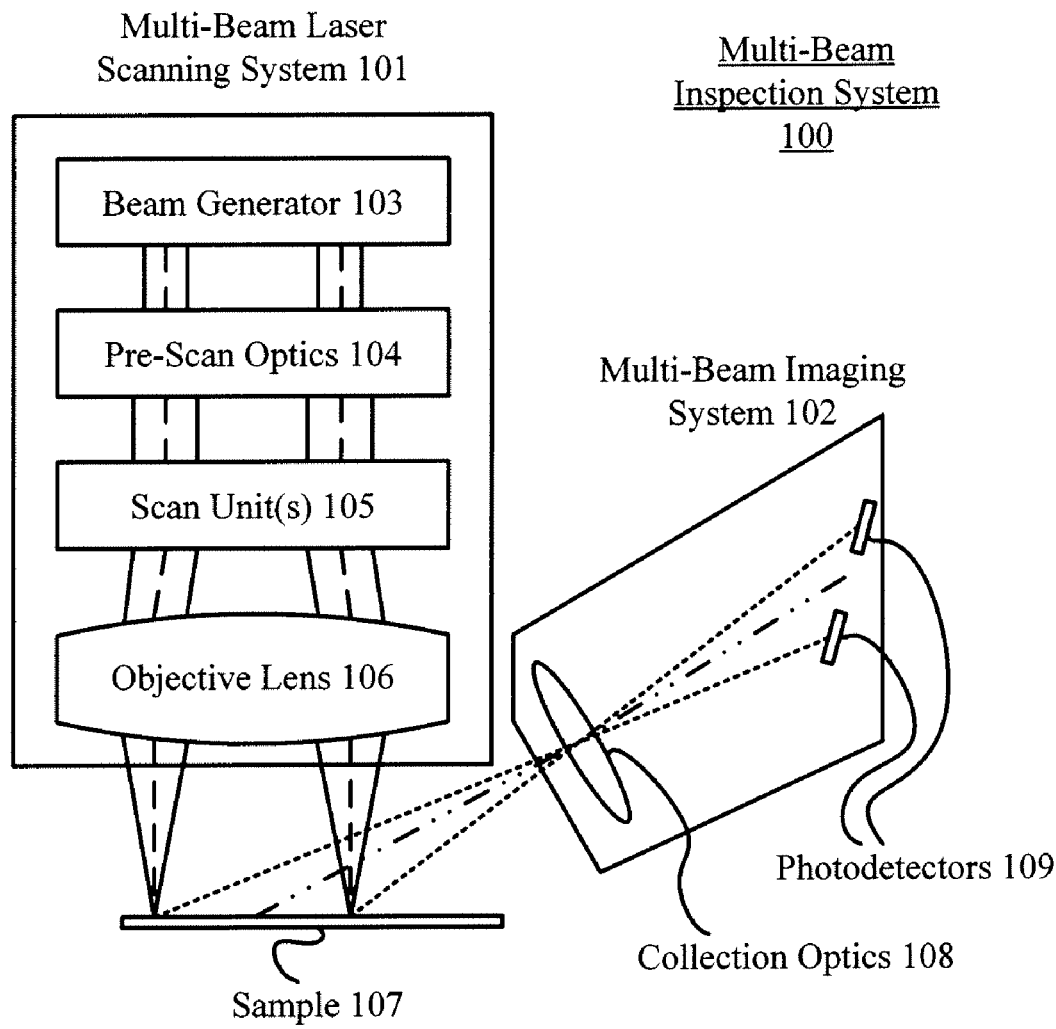
FIG. 1 illustrates a prior art, multi-beam scanning system.
Figure 2:
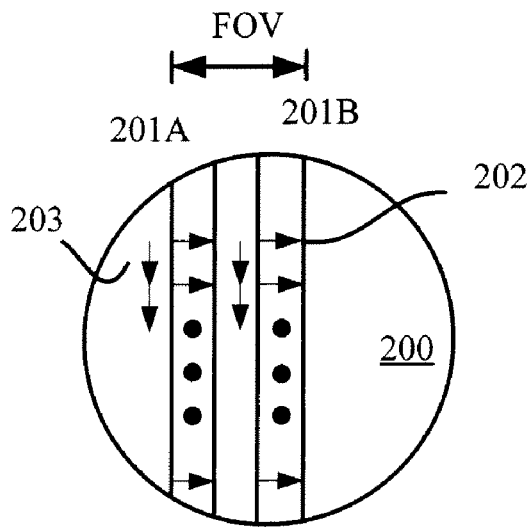
FIG. 2 illustrates a prior art scanning technique that divides a field of view (FOV) by the number of spots in the scanning technique.
Figure 3A:
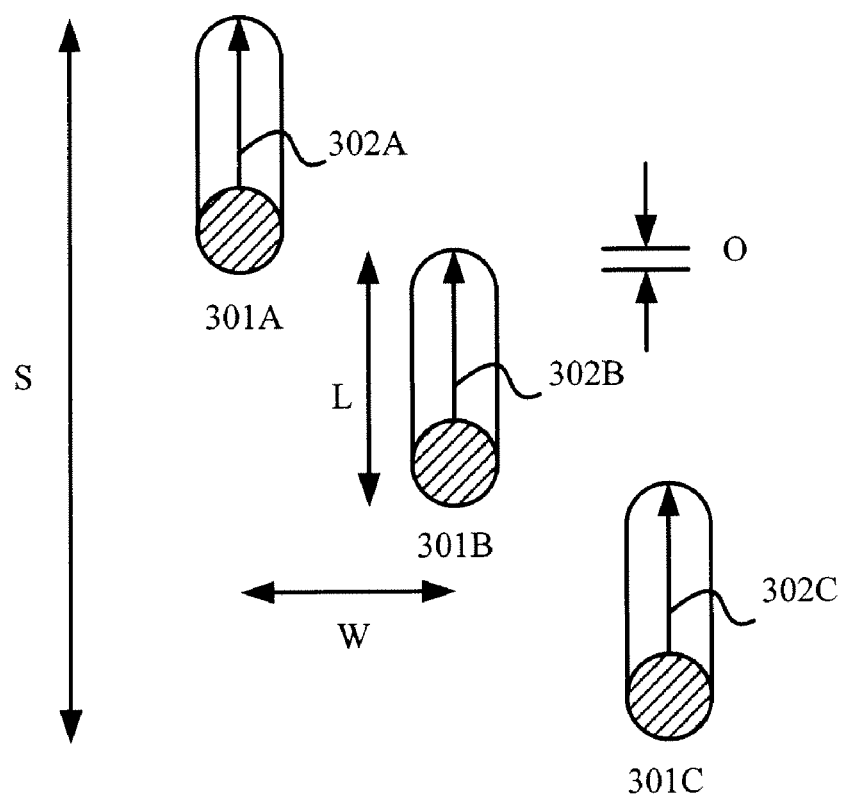
FIGS. 3A and 3B illustrate a prior art scanning technique that uses offset spots scanned in a serpentine pattern.
Figure 3B:
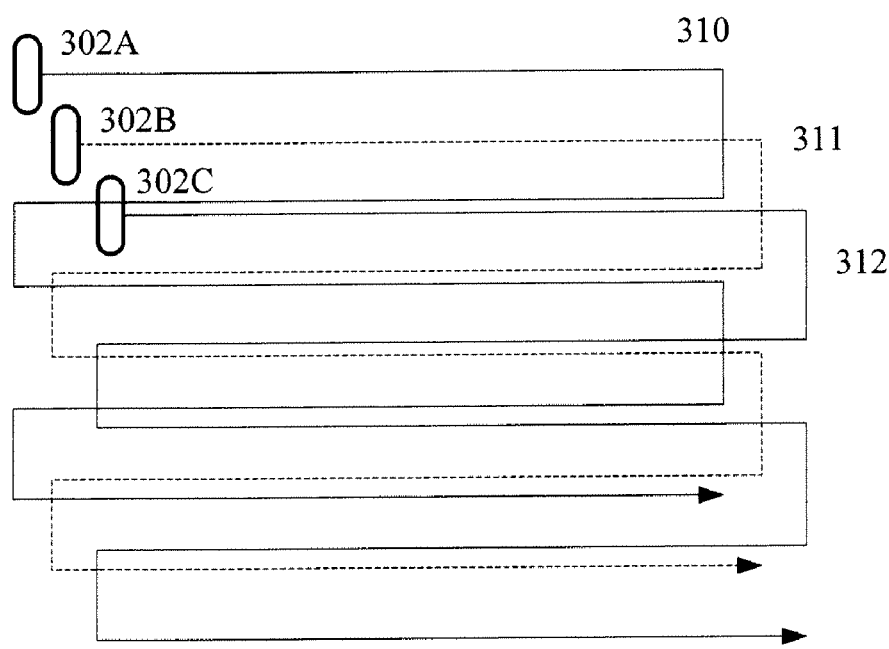
Figure 4:
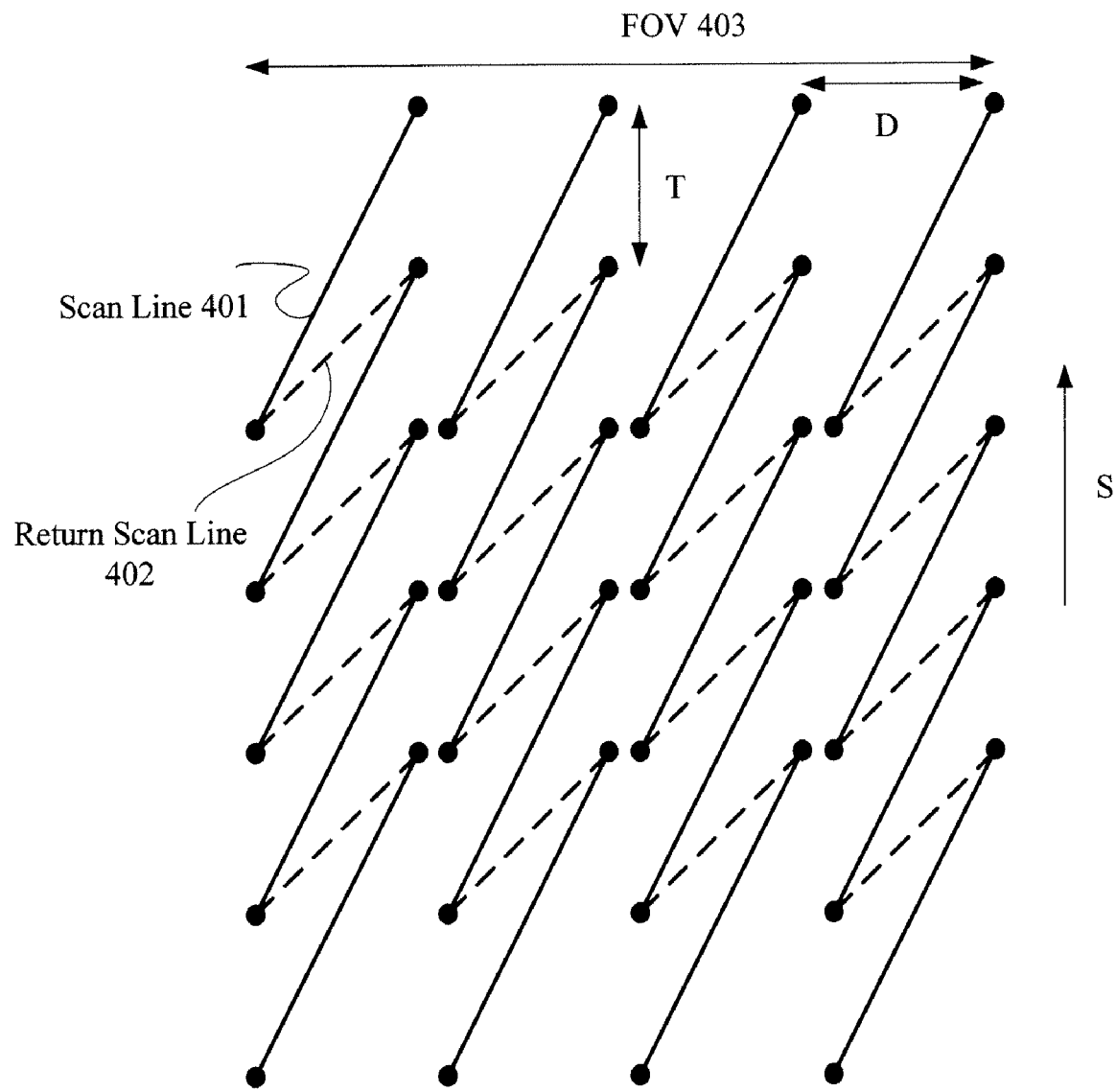
FIG. 4 illustrates a prior art scanning technique that divides an FOV by the number of spots and scans in a pattern not perpendicular to the movement of the wafer.
Figures 5A, 5B:
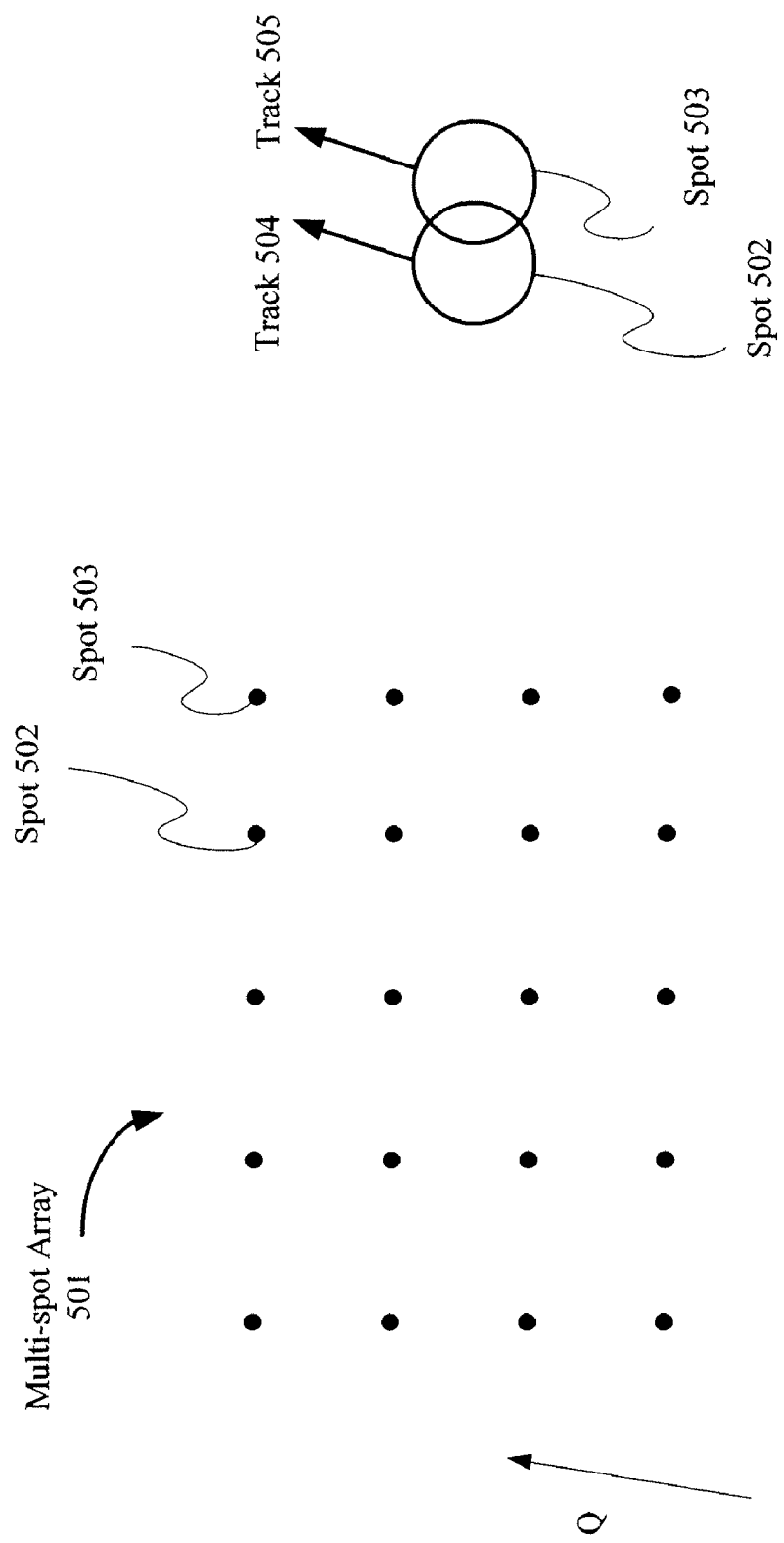
FIGS. 5A and 5B illustrate a prior art scanning technique that uses a multi-spot array with overlapping spots at the detection plane.
Figure 6:
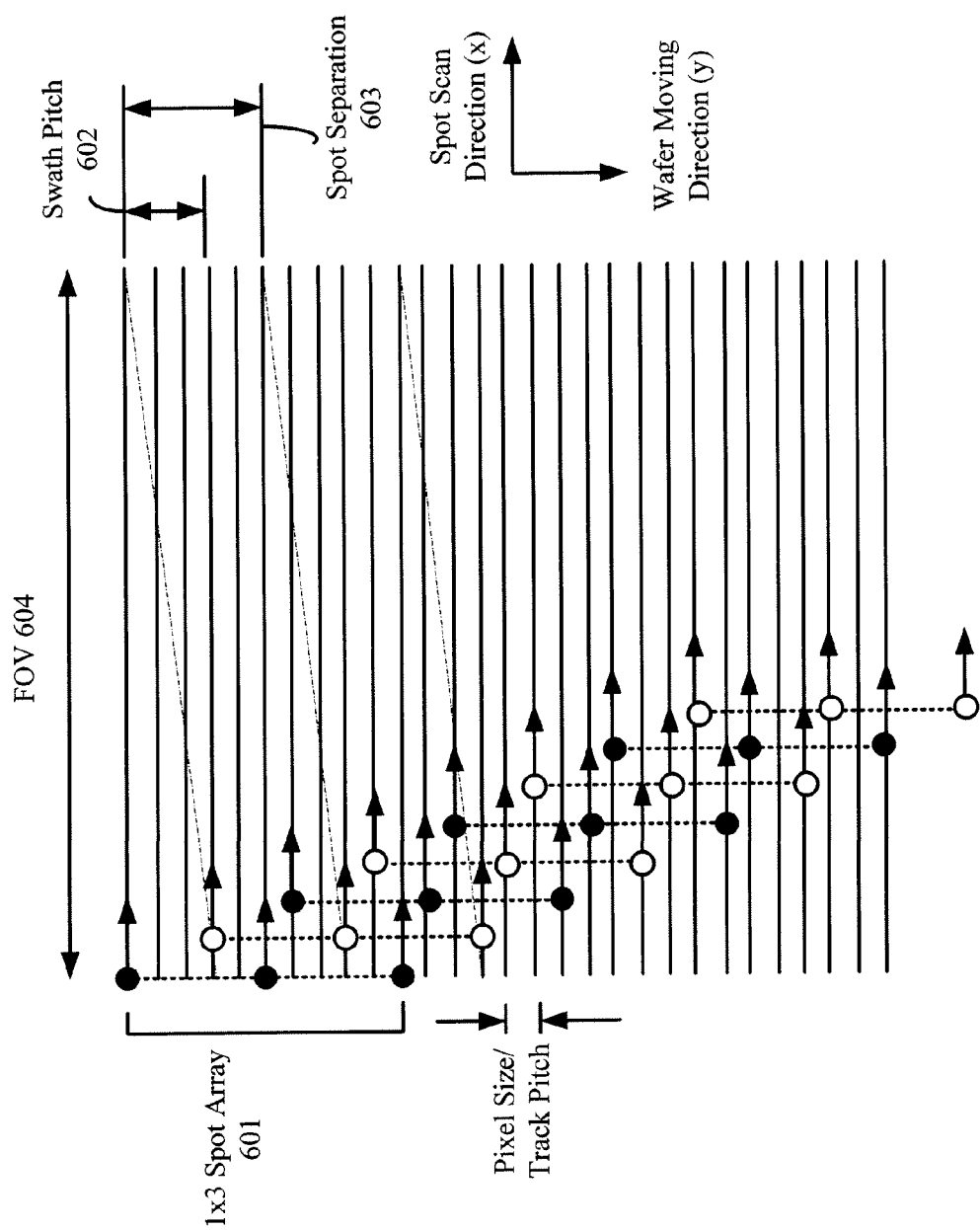
FIG. 6 illustrates an exemplary multi-spot scanning technique using a one-dimensional (1D) spot array having gaps between the spots.

FIG. 6 illustrates an exemplary multi-spot scanning technique using a one-dimensional (1D) spot array having gaps between the spots. In this example, the spot array includes three spots, although actual implementations can use significantly more spots (e.g. tens to hundreds). As shown in FIG. 6, a 1×3 spot array 601 is aligned along a line (shown as a dotted line) that is parallel to the wafer moving direction (y). Spot array 601 scans the wafer in the spot scan direction (x) (which is perpendicular to the wafer moving direction) until the total field of view (FOV) 604 is scanned. Notably, each spot traverses the total FOV 604 (spots of various line scan cycles are shown offset to clearly indicate different cycles). Note that the actual scan direction of spots has a tilt angle with the x direction of the wafer so that the scanning tracks of spots on wafer are exactly in the x direction when wafer moves at a constant speed in the y direction. The tilt angle (shown by the dash-dot line in FIG. 6) is given by $\sin^{-1}(V_1/V_2)$, where $V_1$ is the speed of wafer moving in the y direction and $V_2$ is the speed of spot scan in scan direction. The fly-back of spots can be instantaneous by using scanners such as polygon mirror scanners or acoustic-optical deflector (AOD) scanners.

In this embodiment, the pixel size in the y direction is the spacing between tracks, the spacing between the spots (i.e. the spot separation 603) can be 5 times the pixel size (or track pitch) in y (i.e. 5 tracks), and the spot array line scan pitch 602 in y (that is, the distance the wafer moves in y between line scan cycles) is 3 times the spot size (i.e. 3 tracks). Note that although 8 scan line cycles are shown from left to right (the spot array shown with either black or white spots for ease of reference for each scan line cycle), actual implementations typically include more scan line cycles, e.g. sufficient to reach the end of a swath designated by a user or by a scanning system. In one embodiment, the swath can be designated as crossing an entire wafer.

One advantage of this multi-spot scanning technique is that spot separation 603 can be very (nearly arbitrarily) large so that the spots can be easily separated at the detector plane. Although this spot separation causes scan gaps at the beginning, these scan gaps can be advantageously filled during subsequent scan line cycles. Note that some scan gaps at the beginning of the scan (e.g. see the second, third, and fifth tracks in FIG. 6) and at the end of the scan are not filled despite subsequent line scans. Therefore, in one embodiment, the scan can actually be started and be ended outside a desired scan area, thereby ensuring a complete scan of the desired scan area. Another advantage of this multi-spot scanning technique is that all spots can advantageously scan the full optical FOV. Therefore, the line rate of scanner can be efficiently minimized while still using a large number of spots.

Figure 7A:
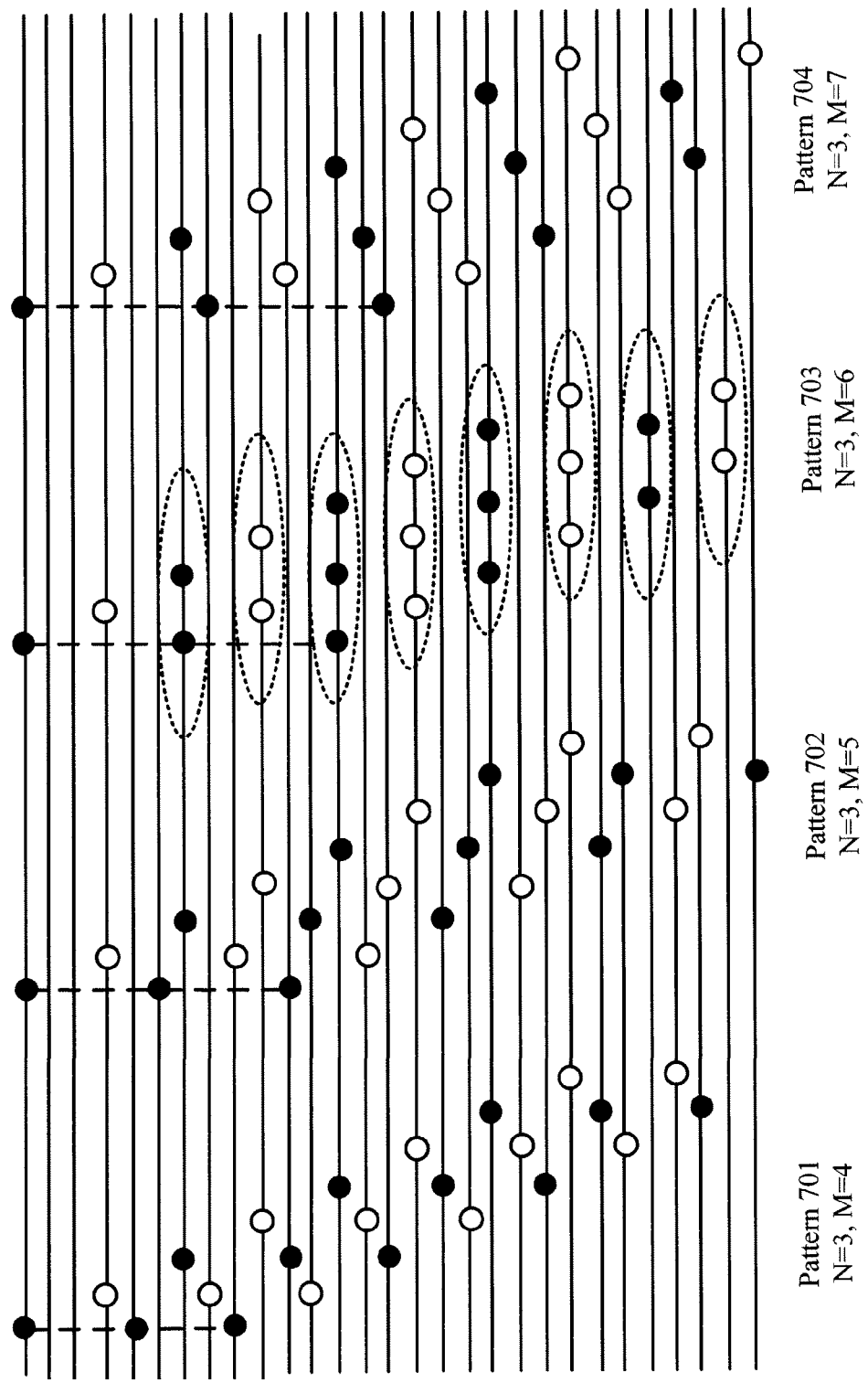
FIG. 7A illustrates four spot patterns that have the same number N of spots in the spot array, but different inter-spot spacing M.

In accordance with one embodiment, the spot separation can be selected to ensure that there are no overlapping or missing tracks. FIG. 7A illustrates four spot patterns 701,

702, 703, and 704 that have the same number N of spots in the spot array, but different spot separation M. Specifically, pattern 701 has 3 spots and a spot separation of 4, pattern 702 has 3 spots and a spot separation of 5, pattern 703 has 3 spots and a spot separation of 6, and pattern 704 has 3 spots and a spot separation of 7.

As shown in FIG. 7A, pattern 703 results in significant numbers of both overlapping and missing tracks. An overlapping track, i.e. a track that is scanned by more than one spot, is indicated by a dotted ellipse. In contrast, patterns 701, 702, and 704 result in no missing tracks (i.e. with the exception of a few tracks at the beginning, the remainder of the missing tracks can be subsequently filled during the scan) and no overlapping tracks.

For equally spaced spots, a necessary (but not sufficient by itself) condition of zero overlapping/missing tracks requires that the swatch pitch (defined as the number of tracks the wafer moves in the y direction from one swath to the next swath) equals the number of spots within one spot array. The reasoning for deriving the sufficient condition for zero overlapping/missing tracks is as follows. Because each swath has N spots to cover N tracks and the spot separation is M, the gaps between the spots need to be filled by a total number of M swathes (including the first swath).

The swathes after the first M swathes may be treated as repeating cycles that are constrained by the same set of rules that apply to the first M swathes. Therefore, only the first M swathes need to be considered for deriving the sufficient condition of a complete scan (which is defined as a completed scanning operation without any overlapping or missing tracks). However, N and M may not be arbitrary numbers even when the scanned tracks of different swathes do not overlap. Additionally, each overlapping track results in one missing track. Therefore, only overlapping cases need to be considered. In other words, the sufficient condition for a complete scan requires that the spots of M consecutive swathes do not overlap with each other. This requirement may be further simplified based on the following reasoning.

If the first spot of second swath does not overlap with any spots of the first swath, then none of the spots of the second swath overlap with any spots of the first swath because the second swath has the same spot pattern as the first swath and is only shifted in the y direction by N tracks. Similarly, if the first spot of the third swath does not overlap with any spots of the first swath, then none of the spots of the third swath overlap with any spots of the first swath because the third swath has the same pattern as the first swath and is only shifted in the y direction by 2N tracks. Note that the non-overlapping requirement for first and second swath applies to any two consecutive swathes. Therefore, for example, none of spots of the third swath overlap with any spots of the second swath.

The above reasoning applies to all M swathes, which leads to the following statement: the sufficient condition for a complete scan requires that none of the tracks covered by the spots of the first swath overlap with any tracks covered by the first spots of the next M−1 swathes (i.e. from the second swath to the $M^{th}$ swath).

Figure 7B:
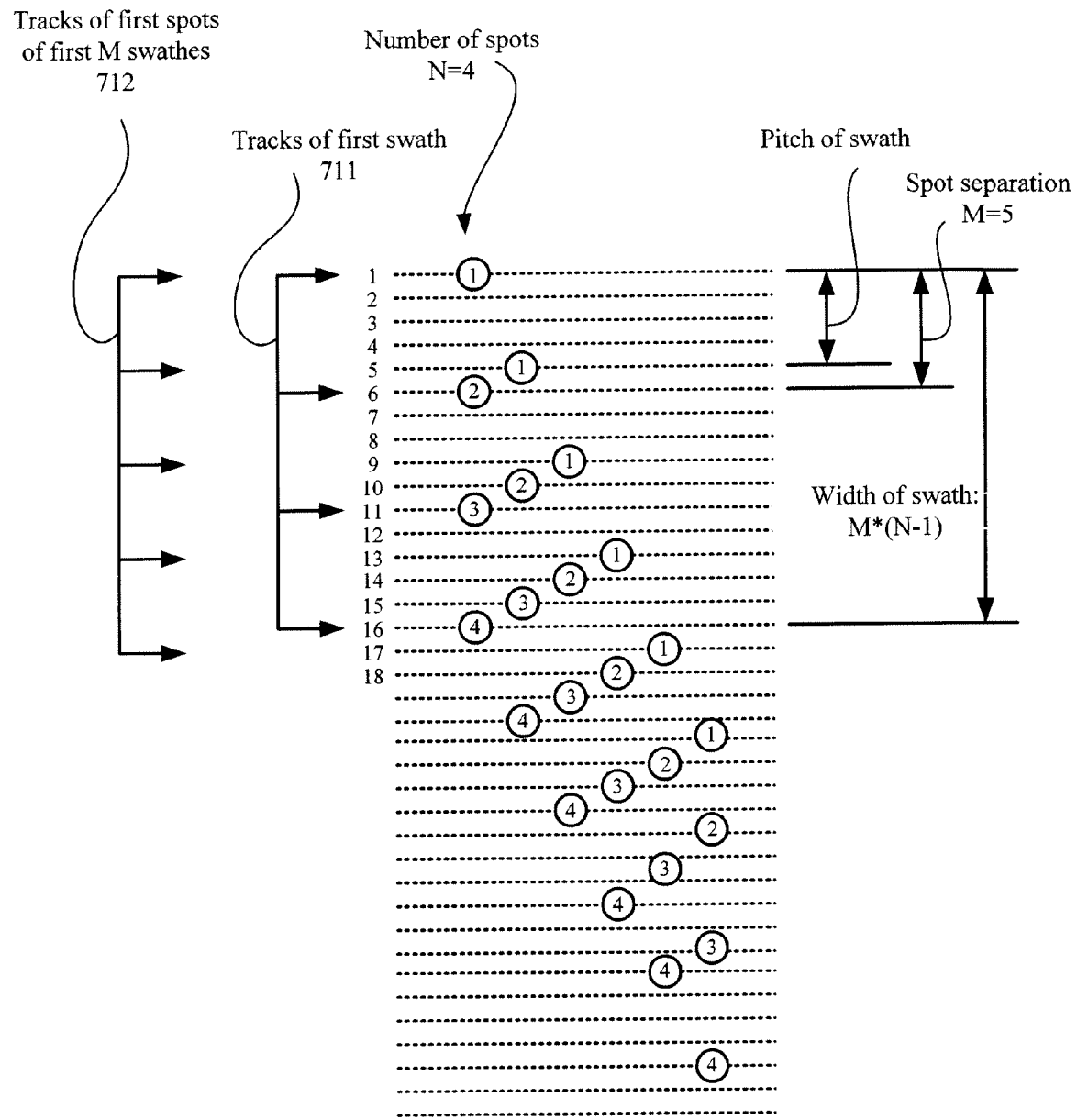
FIG. 7B illustrates an exemplary scan pattern that can result in a complete scan, i.e. no overlapping/missing rows (ignoring a few missing rows at the beginning and at the end of the scan).

The tracks covered by the first swath are given by:

$$K_1 = M(i-1)+1 \quad \text{Equation 1}$$

where i=1, 2, . . . N is the $i^{th}$ spot of the spot array. For example, when N=4 and M=5, as shown in FIG. 7B, the tracks 711 covered by the first swath are 1, 6, 11, and 16.

The tracks covered by the first spots of each swath are given by:

$$K_2 = N(j-1)+1 \quad \text{Equation 2}$$

where j=1, 2, . . . M is the $j^{th}$ swath. For example, as shown in FIG. 7B, when N=4 and M=5, the tracks 712 covered by the first spots of the M swathes are 1, 5, 9, 13, and 17.

The sufficient condition of a complete scan requires that there are no overlapping tracks between any spots of the first swath and the first spots of any of the next M−1 swathes. That is:

$$K_1 \neq K_2 \quad \text{Equation 3}$$

where i=2, 3, . . . N for $K_1$ and j=2, 3, . . . M for $K_2$. For example, when N=4 and M=5, none of the tracks 711 of the first swath (which are 1, 6, 11, and 16) overlap with the tracks 712 of the first spot of the next 4 swathes (which are 5, 9, 13, and 17). Therefore, the scan pattern shown in FIG. 7B can provide a complete scan, i.e. without any overlapping or missing tracks.

Using Equations 1 and 2, Equation 3 can be written as:

$$\frac{M}{j-1} \neq \frac{N}{i-1} \quad \text{Equation 4}$$

where i=2, 3, . . . N and j=2, 3, . . . M. Essentially, Equation 4 states that there are no equals between a first set of M−1 values given by M divided by the integers from 1 to M−1 and a second set of N−1 values given by N divided by the integers from 1 to N−1.

Therefore, the sufficient conditions for a multi-spot scan having N spots with separation M are as follows: (1) the pitch of a swath (in number of tracks) is the same as the number of spots and (2) M and N satisfy Equation 4.

Allowable combinations of the number of spots N and the spot separation M may be found by using a table 730 as shown in FIG. 7C. In table 730, the top-most row (first row) lists the spot index i, the left-most column (first column) lists the spot separation M, and the other entries in table 730 are track indexes $K_1$ of the spots of the first swath calculated from Equation 1. Note that because Equation 2 has the same form as Equation 1, table 730 can also be interpreted as the track index $K_2$ calculated from Equation 2. In this case, the first row lists the swath index j and the first column lists the number of spots N. For example, if the number of spots is 10 (N=10), then the numbers in the row of N=10 (i.e. 1, 11, 21, 31, 41, 51, 61, 71, . . . ) are the tracks covered by the first spots of the $i^{th}$ swath.

To determine if a spot separation M is allowed for a given number of spots N, two sets of numbers in the rows corresponding to M and N are compared. For example, assume that the combination of a spot separation of M=6 and a number of spots of N=10 is to be analyzed. In this case, the first ten numbers in row 6 (M=6) (i.e. the tracks covered by all ten spots of the $1^{st}$ swath) and the first six numbers in row 10 (N=10) (i.e. the tracks of the first spots of the $1^{st}$ to the $6^{th}$ swath) can be considered (shown as squares with filler in FIG. 7C). The tracks covered by the 10 spots of the first swath are 1, 7, 13, 19, 25, 31, 37, 43, 49, and 55 (see M=6). The tracks covered by the first spots of the $1^{st}$ to the $6^{th}$ swathes are 1, 11, 21, 31, 41 and 51. Note that the track covered by the $1^{st}$ spot on the $1^{st}$ swath is indicated by both rows 6 and 10 and therefore can be ignored.

Figure 7D:
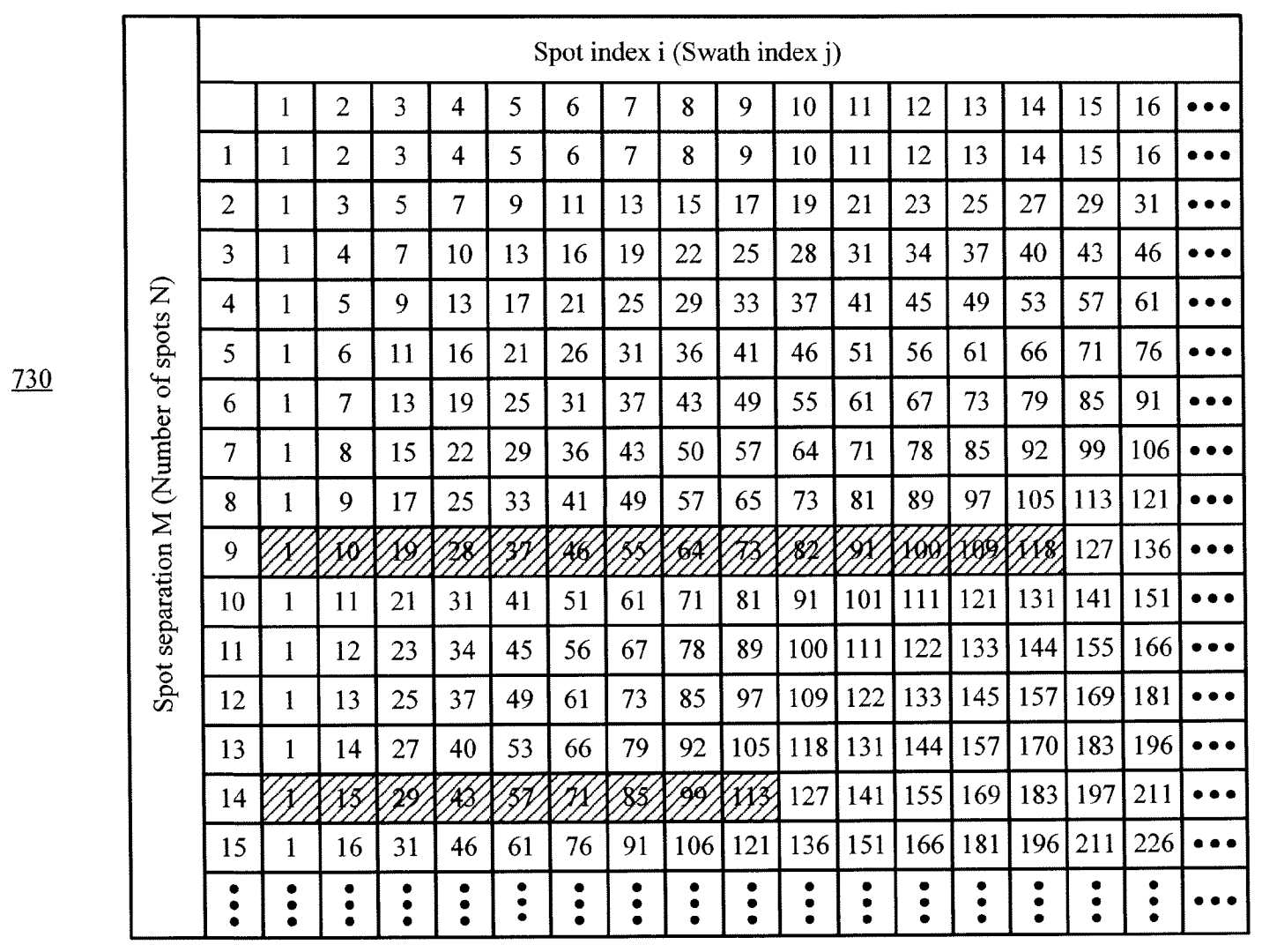

At this point, the remaining numbers can be compared for any overlap. Notably, any number in common between the rows will indicate overlapping/missing tracks in the scan. Because the number 31 appears in both set of numbers (as a result of overlap between the first spot of the $4^{th}$ swath and the $6^{th}$ spot of the first swath), the combination of 10 spots with a spot separation of 6 is not allowed. FIG. 7D shows that another combination of a number of spots N=14 and a spot separation M=9 is allowable because no numbers (i.e. tracks) are in common.

Note that a number of rules to exclude certain combinations of M and N can be derived from Equation 4. For example, the scan is not a complete scan (i.e. has overlapping/missing tracks) if both N and M are even numbers. This result is due to the fact that, when both M and N are even numbers, at least one number (i.e. 2, a result of both M divided by M/2 and N divided by N/2) is found in both the left-hand side and right-hand side of Equation 4. This violates the condition of Equation 4 and therefore results in overlapping (and missing) tracks.

Another example of a combination of M and N that violates Equation 4 is when one of M and N is an integer multiple of the other. For example, if M>N and M=n*N where n is an integer, then N/(N−1) is common to both sides of Equation 4. The same argument applies when N>M and N=n*M (where n is an integer) and M/(M−1) can be found in both sides of Equation 4. As noted above, this violates the condition of Equation 4 and therefore results in overlapping (and missing) tracks.

Figure 7E:
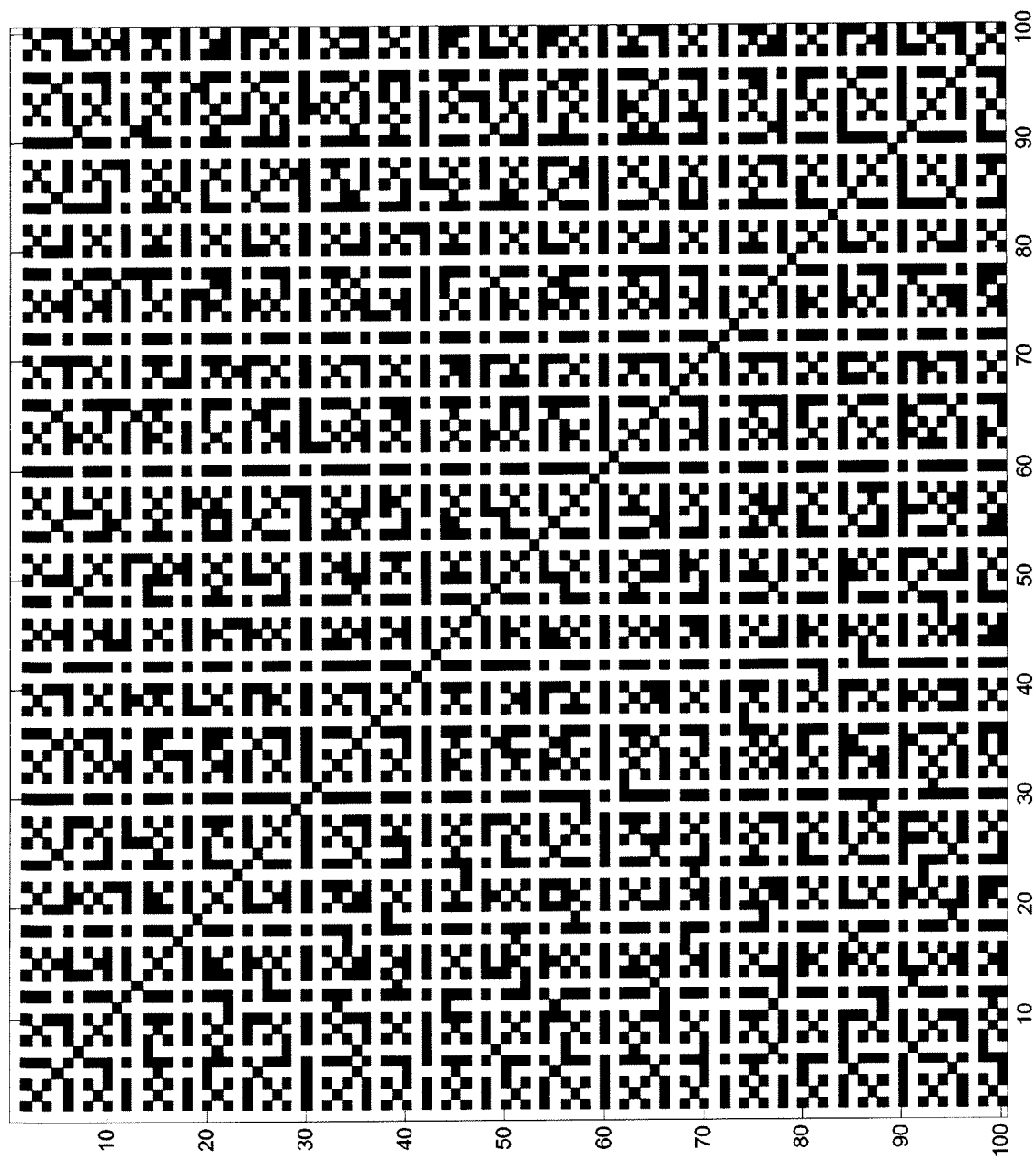
FIG. 7E illustrates a chart that indicates the allowability of M and N combinations, wherein a white pixel at (M,N) represents that that combination of M and N does not result in any overlapping or missing tracks (i.e. is allowable), and a black pixel represents that that combination of M and N results in overlapping or missing tracks (i.e. is not allowable).

FIG. 7E illustrates the results of evaluating Equation 4 with a computer program. In chart 740, the x- and y-axes are M=2:100 and N=2:100, respectively, and a white pixel at (M,N) represents that that combination of M and N does not result in any overlapping/missing tracks (i.e. is allowed), and a black pixel represents that that combination of M and N results in overlapping/missing tracks (i.e. is not allowed).

Note that, in general, combinations of (M,N) using prime numbers (wherein a prime number is only divisible by 1 and itself) do not result in any overlapping/missing tracks (subject to the integer multiple limitation discussed in the previous paragraph). For example, for a spot separation of M=11, any number of spots can satisfy Equation 4 as long as the number is not a multiple of 11. For 97 spots (N=97), any spot separation can satisfy Equation 4 as long as it is not a multiple of 97. Thus, finding allowable combinations of M and N can be quickly evaluated using Equation 4, or determined by reference to either a table (see, e.g. table 730 of FIGS. 7C and 7D) or a chart (see, e.g. chart 740 of FIG. 7E). Evaluation of Equation 4 can be performed by a computer or other computational device and table 730 or chart 740 can be stored in any storage medium (e.g. a memory accessible by a computer or other device).

Note that the above-described principles can be equally applied to two-dimensional (2D) spot arrays. For example, a spot array on a square grid can be mathematically transformed into an equivalent 1D spot array by tilting the grid (i.e. at a predetermined angle) such that the spots are equally spaced in the direction perpendicular the spot scan direction. FIG. 8A illustrates an exemplary 2D spot array 803 (in this case, a 3×3 array) having an equivalent 1D spot array 804. Once again, the spot separation 805 (in the direction perpendicular to spot scan direction) is greater than 1 (in the unit of track pitch/pixel size), which advantageously eliminates crosstalk at the detector plane. In this case, 2D spot array (3×3) 803 has an equivalent 1D spot array (1×9) having a spot separation 805 of 4.

In 2D spot array 803, the actual spacing between spots is given by:

$$D=M/\sin\theta$$

where $\theta$ is the tilt angle of the 2D spot grid, which is given by $\tan\theta=1/N$ for an N×N square spot array.

Figure 8B:
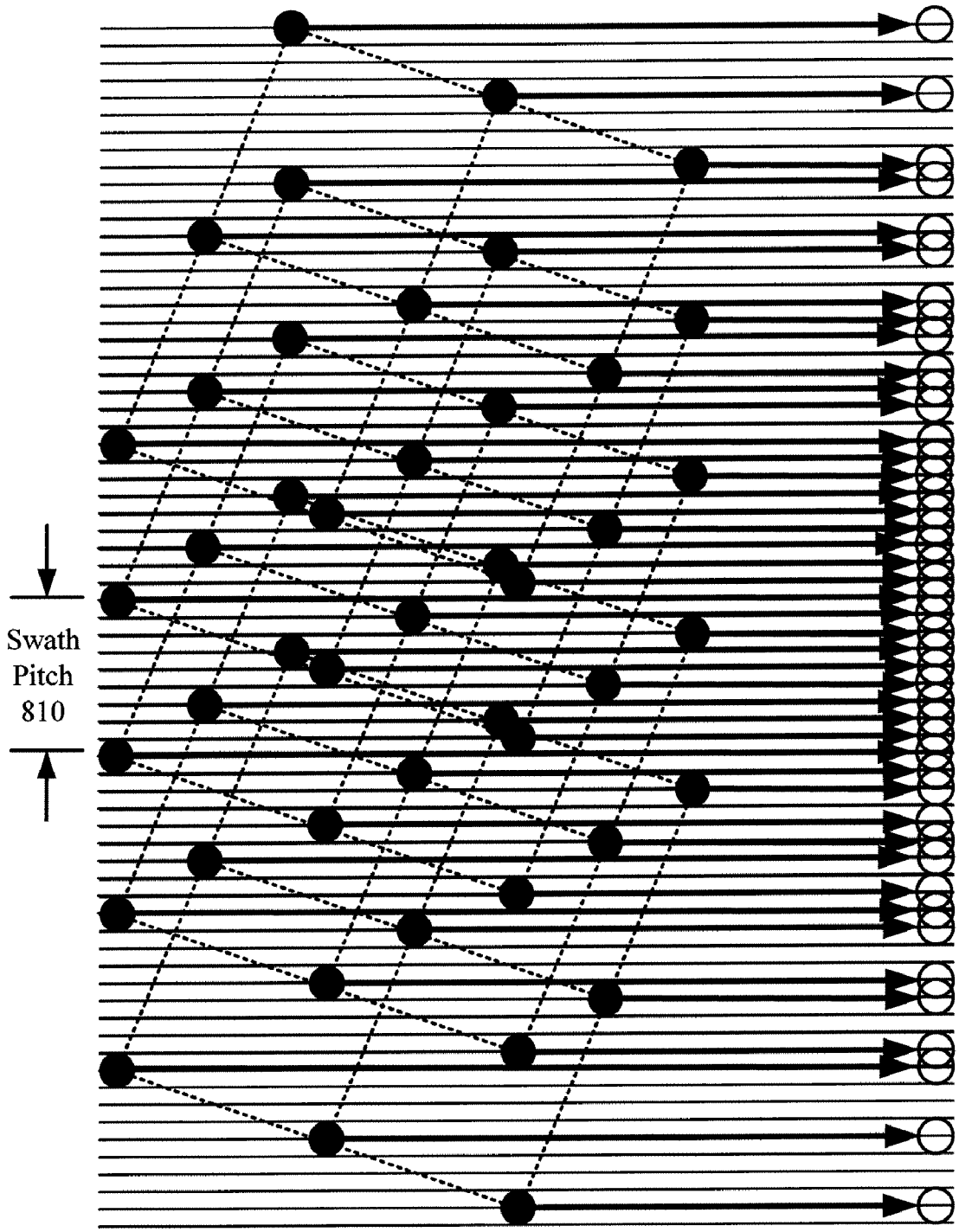
FIG. 8B illustrates that the gaps of scanned tracks between spots shown in FIG. 8A are filled in gradually based on subsequent scan line cycles.

Referring to FIG. 8B, the gaps of scanned tracks between spots shown in FIG. 8A are filled in gradually based on subsequent scan line cycles. There are 5 consecutive scan line cycles of 2D spot array 801 shown in FIG. 8B to demonstrate that the gaps between spots can be filled by the scan line cycles without generating any overlapping tracks. As noted above, a swath pitch 810 is equal to the total number of spots, which in this example is 9. As with the 1D spot array, the scan line cycles can be started (and ended) outside the desired scan area (e.g. just beyond the edge of the wafer, which is already performed in the industry). Therefore, the additional gaps formed by using the 2D spot array (e.g. on the left and right sides) do not affect the desired scan area.

Advantageously, the 2D spot array can facilitate the use of a more compact detector compared to the 1D spot array. Specifically, a detector in a scanning system using the 2D spot array can also be formed in a 2D configuration. This 2D detector configuration can be more compact than a 1D configuration. Therefore, even though both the 1D and 2D embodiments advantageously use the full FOV, the 2D embodiment may provide some additional cost savings by using a more compact detector configuration.

Figure 9A:
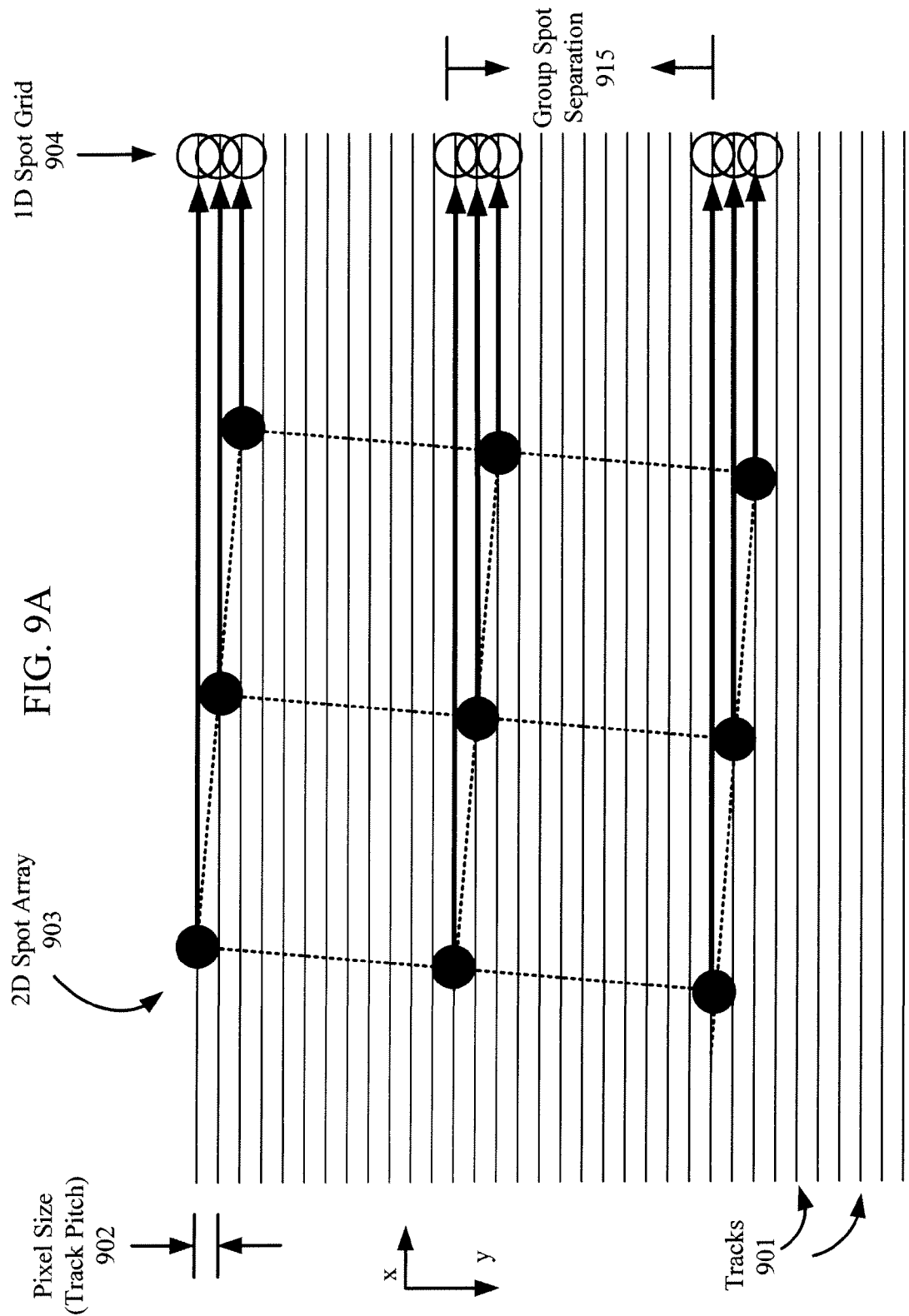
FIG. 9A illustrates an alternative alignment of a 2D spot array in which the detector plane can distinguish between groups of spots.
Figure 9B:
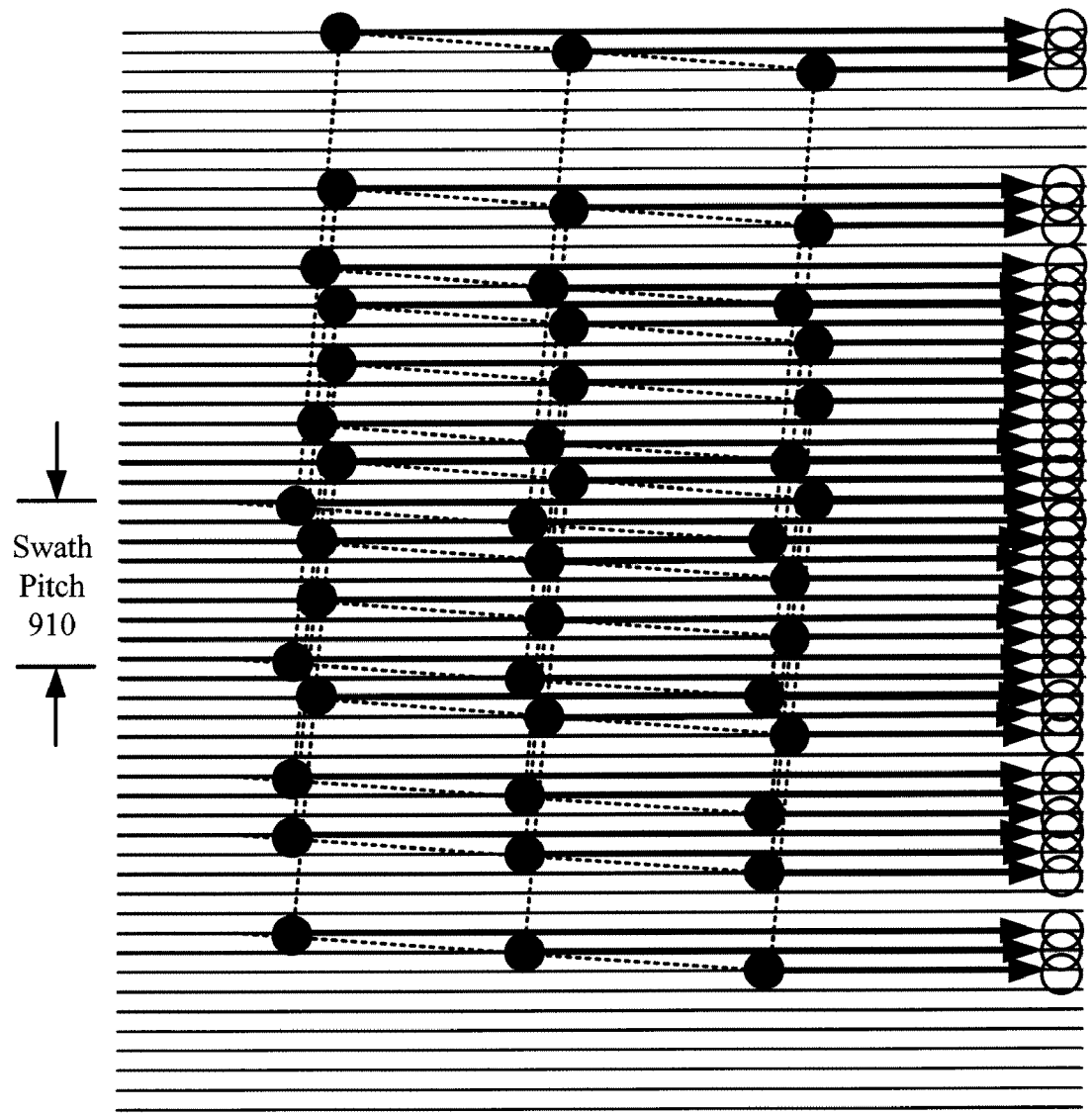
FIG. 9B illustrates several consecutive scan line cycles of the 2D spot array of FIG. 9A to demonstrate that the gaps between spots can be substantially filled by the scan line cycles without generating any overlapping tracks.

FIG. 9A illustrates an alternative alignment of a 2D spot array 903 on tracks 901, which have a pixel size/track pitch 902. In 2D spot array 903, several rows of spots are closely grouped together in a group such that there is no gap between the scan tracks among each group. However, a group spot separation 915 can be provided. This configuration is equivalent to a 1×3 1D spot array 904, with an equivalent y pixel of 3× the actual y pixel size. In other words, this configuration leverages the fact that within each group the detector plane will be unable to distinguish between the contributions of the 3 spots, but will be able to distinguish the contribution from each group. FIG. 9B illustrates several consecutive scan line cycles (having a swath pitch 910) to demonstrate that the gaps between spots can be substantially filled by the scan line cycles without generating any overlapping tracks.

Notably, although only a small number of spots are shown in the figures to clearly demonstrate spacing, filling, and no overlapping, other embodiments can advantageously use a large number of spots to achieve high speed inspection. For example, a 1D array of 32 to 64 spots can be implemented to achieve a total data rate of 6.4 GPPS to 12.8 GPPS with a data rate of 200 MPPS per channel. Similarly, a 10×10 2D array can achieve 20 GPPS. The number of spots can scale up to even larger numbers as the resolution increases.

Figure 10:
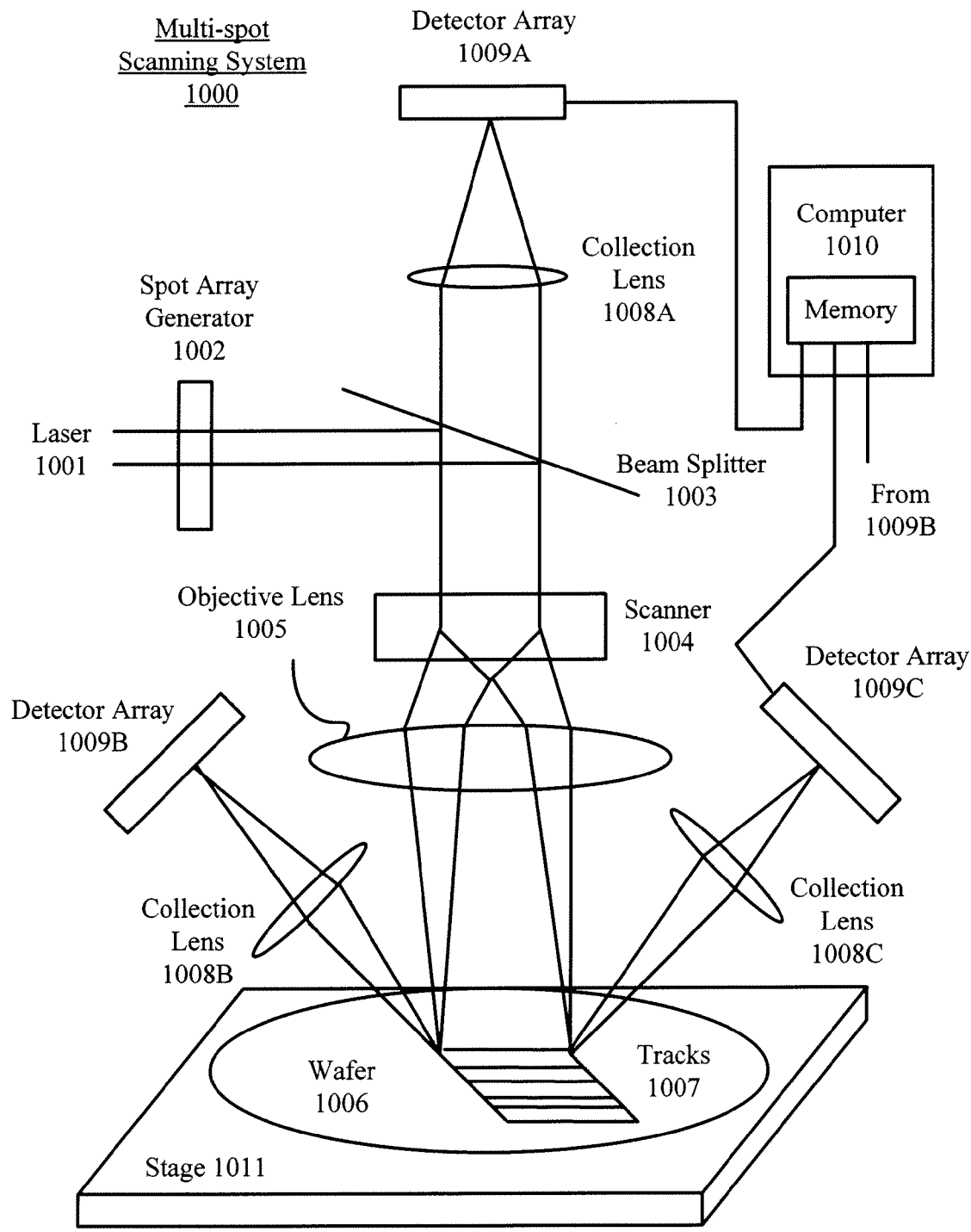
FIG. 10 illustrates one embodiment of a multi-spot scanning system that can use a multi-spot scanning technique using a spot array having gaps between spots.

FIG. 10 illustrates one embodiment of a multi-spot scanning system 1000. System 1000 includes a spot array generator 1002 that creates a desired 1D/2D spot array from a beam output by laser 1001. In one embodiment, spot array generator 1002 can include a diffractive optical element to create the desired spot array and the spacing between spots of the array (both of which can be designated by a user or automatically by a system while conforming to the above-described equations). A beam splitter 1003 reflects the spot array to a scanner 1004, which in turn provides the spot array to an objective lens 1005. Objective lens 1005 focuses the spot array onto a wafer 1006. System 1000 uses scanner 1004 (which moves in an x direction) and wafer 1006 (which is moved in a y direction using a stage 1011) to scan a plurality of tracks 1007 on wafer 1006. Collection lens 1008A, 1008B, and 1008C collect the light scattered and/or reflected by wafer 1006 during the scan of tracks 1007 and focus that light onto detector arrays 1009A, 1009B, and 1009C, respectively. (Note that after the light is reflected by wafer 1006, some of the reflected light passes back through objective lens 1005 and scanner 1004 to impinge on beam splitter 1003. At this point, the beam splitter transmits a portion of the light in the form of collimated beams to collection lens 1008A, which in turn focuses the light onto detector array 1009A.)

Figure 11:
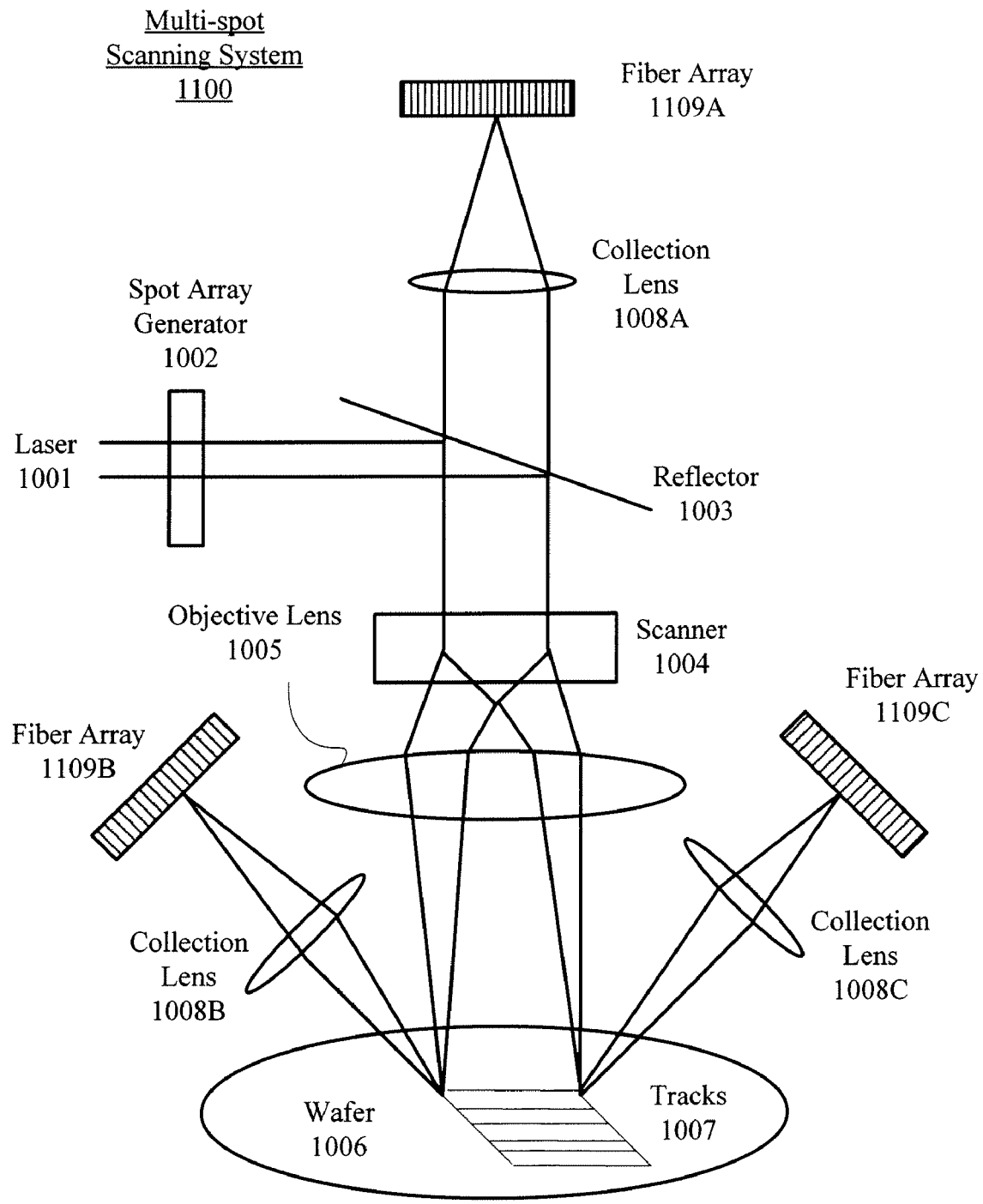
FIG. 11 illustrates another embodiment of a multi-spot scanning system that can use a multi-spot scanning technique using a spot array having gaps between spots. This embodiment includes fiber arrays instead of detector arrays (FIG. 10).
Figure 12:
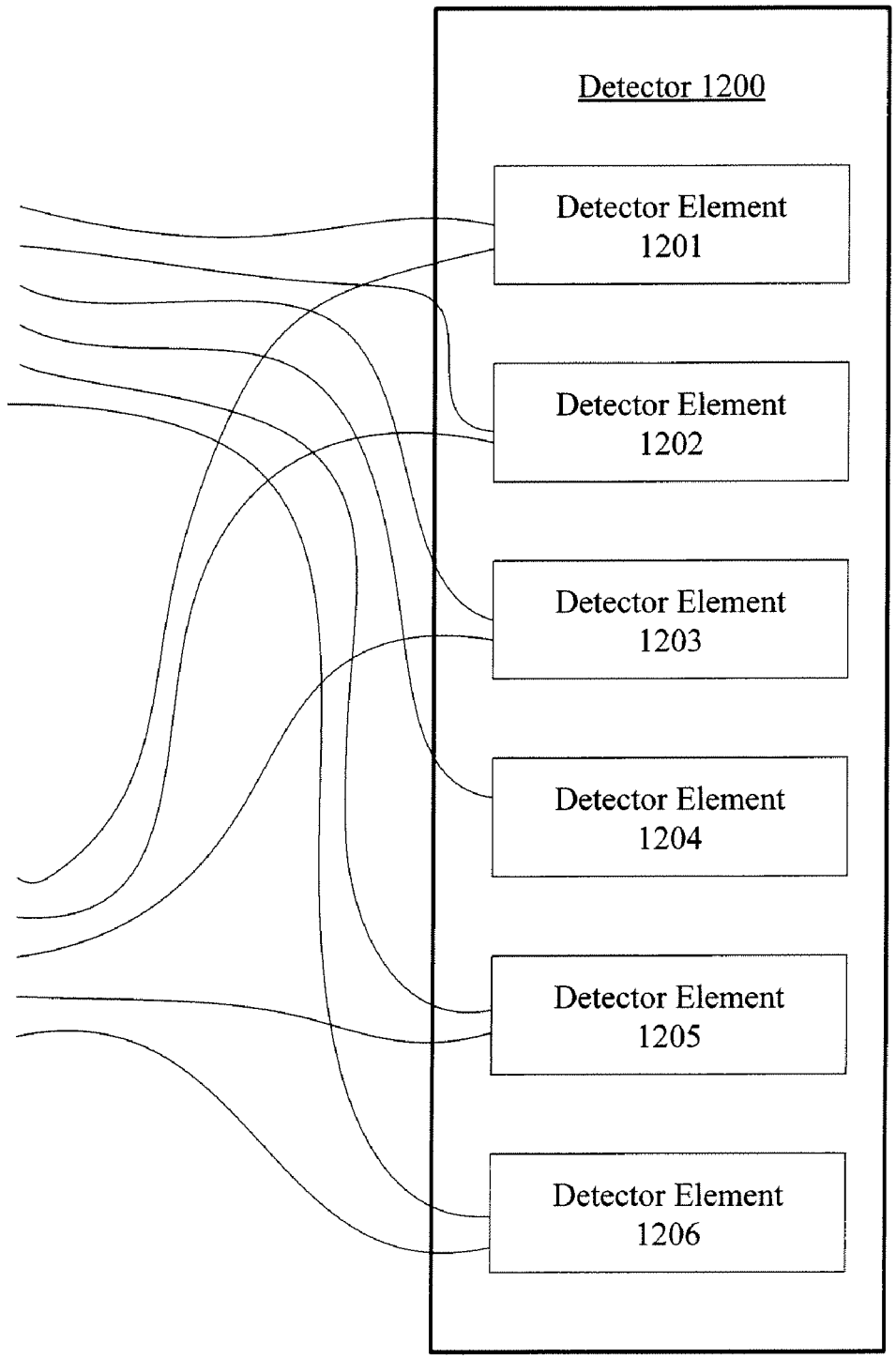
FIG. 12 illustrates a configuration for a detector that, depending on the optimization of sensitivity to specific samples, allows the optical signals collected by the fiber arrays (FIG. 11) to be either combined together in detector elements or switched between them.

System 1000 can use various imaging modes, such as bright field, dark field, and confocal. For example, in one embodiment, detector array 1009A generates a bright field image (which detects reflected light), whereas detector arrays 1009B and 1009C generate dark field images (which detect scattered light). A pinhole array that matches the layout of the illumination spot array can be placed in front of each detector array 1009 to generate confocal image. U.S. Pat. No. 6,208, 411, which is incorporated by reference herein, describes these imaging modes in further detail. In one embodiment, detector arrays 1009A, 1009B, and 1009C can be replaced by fiber arrays 1109A, 1109B, and 1109C, which are shown in a multi-spot scanning system 1100 in FIG. 11. FIG. 12 illustrates a configuration for a detector 1200 that, depending on the optimization of sensitivity to specific samples, allows the optical signals collected by the fiber arrays (e.g. fiber arrays 1109B and 1109C) to be either combined together in detector elements 1201-1206 or switched between them.

Referring back to FIG. 10, an image of the scanned area can be obtained by re-arranging the outputs from the plurality of channels (e.g. from each of detector arrays 1009A-1009C (or from each of fiber arrays 1109A-1109C in FIG. 11)), which have been stored in a memory of a computer 1010. Advantageously, this memory is only slightly more that what would be required to store the swath length covering at least 2 to 3 dice for die-to-die comparison. This computer 1010 and associated memory can be used in other multi-spot scanning systems (e.g. multi-spot scanning system 1100 (not shown for simplicity)).

The above-described multi-spot scanning system can advantageously use a large number of spots for an x-y raster scan, thereby allowing a high scan speed and providing a high sensitivity inspection. Moreover, because of the spacing between spots and the resulting clean separation of spots on the detection plane, this multi-spot scanning system can eliminate cross-talk. Yet further, the described multi-spot scanning system can advantageously traverse the full FOV, thereby fully leveraging the use of optics providing the FOV. Traversing the full FOV facilitates smooth and continuous motion of the scanner and the stage.

Although illustrative embodiments of the invention have been described in detail herein with reference to the accompanying figures, it is to be understood that the invention is not limited to those precise embodiment. They are not intended to be exhaustive or to limit the invention to the precise forms disclosed. As such, many modifications and variations will be apparent to practitioners skilled in this art.

For example, another implementation could include a 2D spot array for a spiral scan. Note that such a spiral scan would need re-alignment of adjacent tracks (e.g. performed by the computer). Therefore, this implementation would require nearly perfect registration between tracks and tight tolerance to the environmental stability such as vibration and stage error.

Figure 13:
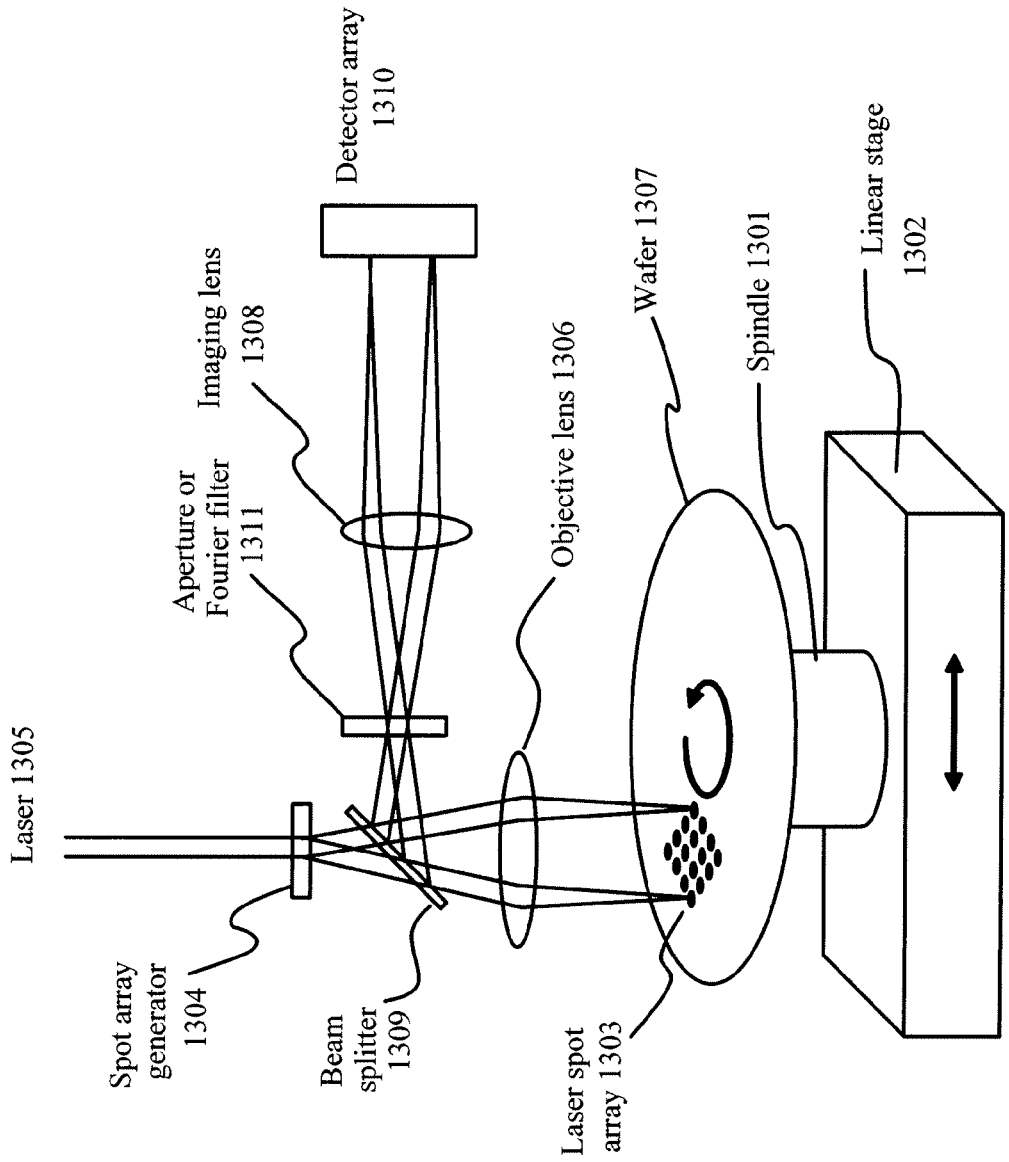
FIG. 13 illustrates another embodiment of a multi-spot scanning system that provides a spiral scan.

FIG. 13 illustrates an embodiment of a multi-spot spiral scanning system 1300. A spiral scan can be accomplished by moving a wafer 1307 using a spindle 1301 and a linear stage 1302, while a laser spot array 1303 remains stationary. System 1300 can include a spot array generator 1304 that can create a desired 1D/2D spot array from a beam output by a laser 1305. In one embodiment, spot array generator 1304 can include a diffractive optical element to create the desired spot array and the spacing between spots of the array (both of which can be designated by a user or automatically designated by a system while conforming to the above-described equations). An objective lens 1306 focuses the spot array onto the wafer 1007. Imaging lens 1308 images the spot array at wafer surface and reflected by the beam splitter 1309 onto a detector array 1310. An aperture or Fourier filter 1311, which can rotate in synchronism with the wafer, is placed at the back focal plane of objective lens 1306. Various imaging modes such as bright field, dark field, and phase contrast can be implemented by using different apertures or Fourier filters. U.S. Pat. Nos. 7,295,303 and 7,130,039, which are incorporated by reference herein, describe these imaging modes in further detail.

Accordingly, it is intended that the scope of the invention be defined by the following claims and their equivalents.

The invention claimed is:

1. A multi-spot scanning method comprising:
   selecting a number of spots N for a one-dimensional (1D) spot array;
   determining a separation M between the spots in the spot array to minimize crosstalk;
   performing a scan on a wafer using the spot array and a full field of view (FOV) for each scan line cycle;
   performing a complete scan without overlapping/missing tracks by providing that:
   a pitch of a swath of the array equals the number of spots N; and $$\frac{M}{j-1} \neq \frac{N}{i-1}$$

where i=2,3, . . . N and j=2,3, . . . M,
   wherein performing the complete scan includes performing a plurality of scan line cycles, each scan line cycle filling in gaps left by previous scan line cycles; and
   using a table to determine allowable combinations of M and N, the table being organized using (1) a spot index i and the separation M, or (2) a swath index j and the number of spots N.

2. A multi-spot scanning method comprising:
   selecting a number of spots N for a one-dimensional (1D) spot array;
   determining a separation M between the spots in the spot array to minimize crosstalk;
   performing a scan on a wafer using the spot array and a full field of view (FOV) for each scan line cycle;
   performing a complete scan without overlapping/missing tracks by providing that:
   a pitch of a swath of the array equals the number of spots N; and $$\frac{M}{j-1} \neq \frac{N}{i-1}$$

where i=2,3, . . . N and j=2,3, . . . M,
   wherein performing the complete scan includes performing a plurality of scan line cycles, each scan line cycle filling in gaps left by previous scan line cycles; and
   using a chart to determine allowable combinations of M and N, the chart including pixels, wherein a first color pixel indicates overlapping/missing tracks and a second color pixel indicates lack of overlapping/missing tracks.

3. A multi-spot scanning method comprising:
   selecting a number of spots N for a two-dimensional (2D) spot array;

determining a separation M between groups of spots in the 2D spot array to minimize crosstalk; and performing a scan on a wafer using the 2D spot array and a full field of view (FOV) for each scan line cycle, wherein a spacing D between spots is given by M/sin θ, where θ is a tilt angle of the 2D spot array.

4. The multi-spot scanning method of claim 3, wherein performing the scan includes performing a plurality of scan line cycles, each scan line cycle filling in gaps left by previous scan line cycles.

5. The multi-spot scanning method of claim 4, wherein the scan is begun and ended outside a desired scan area on the wafer to ensure full scan coverage.

6. The multi-spot scanning method of claim 3, further including performing a complete scan without overlapping/missing tracks by providing that:

a pitch of a swath of the array equals the number of spots N; and $$\frac{M}{j-1} \neq \frac{N}{i-1}$$

where i=2,3, . . . N and j=2,3, . . . M.

7. The multi-spot scanning method of claim 3, further including using a table to determine allowable combinations of M and N, the table being organized using (1) a spot index i and the separation M, or (2) a swath index j and the number of spots N.

8. The multi-spot scanning method of claim 3, further including using a chart to determine allowable combinations of M and N, the chart including pixels, wherein a first color pixel indicates overlapping/missing tracks and a second color pixel indicates lack of overlapping/missing tracks.

* * * * *